United States Patent [19]
Oren

[11] Patent Number: 5,847,241
[45] Date of Patent: *Dec. 8, 1998

[54] PROCESS FOR THE PREPARATION OF P-BROMOFLUOROBENZENE

[75] Inventor: Jakob Oren, Nesher, Israel

[73] Assignee: Bromine Compounds Ltd., Israel

[*] Notice: This patent issued on a continued prosecution application filed under 37 CFR 1.53(d), and is subject to the twenty year patent term provisions of 35 U.S.C. 154(a)(2).

[21] Appl. No.: 697,461

[22] Filed: Aug. 26, 1996

[30] Foreign Application Priority Data

Aug. 28, 1995 [IL] Israel ........................................ 115090

[51] Int. Cl.$^6$ .................................................. C07C 25/13
[52] U.S. Cl. ................................................ 570/147
[58] Field of Search ............................. 570/147

[56] References Cited

FOREIGN PATENT DOCUMENTS

| | | |
|---|---|---|
| 0 492 594 A1 | 1/1992 | European Pat. Off. . |
| 2 012 480 | 3/1970 | France . |
| 62-93244 | 4/1987 | Japan . |
| 2221640 | 9/1987 | Japan ...................................... 570/147 |
| 62-221640 | 9/1987 | Japan . |
| 63-14742 | 1/1988 | Japan . |

OTHER PUBLICATIONS

Scheimann et al., *Chem. Ber.*, 64, 1340 (1931).

Ferguson et al., *J. Am. Chem. Soc.*, 76, 1250 (1954).

Olah et al., *J. Am. Chem. Soc.*, 1823 (1957).

Suter et al., *J. Am. Chem. Soc.*, 63, 602 (1941).

*Primary Examiner*—Alan Siegel
*Attorney, Agent, or Firm*—Lerner, David, Littenberg, Krumholz & Mentlik

[57] ABSTRACT

Process for the production of p-bromofluorobenzene by the bromination of fluorobenzene, characterized in that the bromination is carried out with liquid bromine at temperatures below 0° C.

14 Claims, No Drawings

PROCESS FOR THE PREPARATION OF P-BROMOFLUOROBENZENE

FIELD OF THE INVENTION

This invention relates to a process for the preparation of p-bromofluorobenzene (hereinafter PBFB) in high yield and high purity by the bromination of fluorobenzene (hereinafter FB). More particularly, it relates to a process for the preparation of PBFB of >99.8% purity and in a yield of 98%.

BACKGROUND OF THE INVENTION

The preparation of bromofluorobenzene by different processes has been described in the literature. Thus, the bromination of FB with excess liquid bromine catalyzed by iron filings is described by G. Schiemann et al., "Aromatic fluorine compounds. VIII. Some transformations with PBFB", Chem. Ber. 64, 1340, 1931. 80% PBFB is obtained by this method.

L. N. Ferguson et al., "Bromination of Halobenzenes", J. Am. Chem. Soc., 76, 1250, 1954, describes the bromination of FB with bromine in $CS_2$ at 54°–57° C., using $AlBr_3$, giving an isomeric mixture which contains only 89.1% PBFB.

JP 62 221,640 and JP 62 93,244 describe a method whereby a gaseous mixture of FB, HBr, oxygen and nitrogen is heated over a Cu-Y-type zeolite at 190°–200° C. for 2–3 hours to give 93–98% PBFB at a conversion of 50%.

JP 63 14,742 describes the reaction of bromine with FB (~1:2.7) in the presence of iron powder at 5°–40° C. to yield a mixture of 1.0% o-bromofluorobenzene (hereinafter OBFB), 0.5% metabromofluorobenzene (hereinafter MBFB) and 98.5% PBFB with a low conversion of FB. An attempt to separate the isomers by melt crystallization resulted in PBFB in a purity of 99.8% but in a yield of only 17.2%.

G. Olah et al., "The preparation and examination of organic fluorine compounds. XXIV. The halogenation of fluorobenzene", J. Chem. Soc., 1823–9, 1957,describes the bromination of FB with a molar ratio $Br_2$/FB 0.8:1,whereby a product containing 98.2% PBFB and 1.8% OBFB was obtained after removing unreacted FB in a yield of ~90%. This is still not a satisfactory result as the isomers cannot be separated by distillation. This method involves underbromination of the FB, which then requires the removal and recovery of unreacted FB at the end of the reaction. Also, an isomeric mixture is always obtained under these conditions.

It is seen that the under-bromination according to the prior art gives mainly PBFB accompanied with small, but still excessive, amounts of OBFB and in some cases also MBFB, and generally with unsatisfactory yields.

The use of excess bromine in this reaction has been described, C. M. Suter et al., "Some Fluorinated Amines of the Pressor Type", JACS, 63, 602–5 (1941). The $Br_2$/FB ratio was ~1.27 which converts all the OBFB, and some of the PBFB to dibromofluorobenzene (hereinafter DBFB). This mixture can be separated by fractional distillation. The reported yield in this case was 72% PBFB and >20% DBFB and other impurities.

Due to the unsatisfactory nature of the prior art, we carried out research to try to improve both the purity and the yield of PBFB. We discovered that the reaction temperature has a crucial influence on the ratio of the bromofluorobenzene isomers. Thus by lowering the temperature of the reaction we were able to increase the selectivity towards PBFB. Since very little OBFB is formed during the reaction only a very slight excess of bromine is required to convert this OBFB to DBFB by dibromination (post-reaction). The DBFB can be easily separated by fractional distillation leaving highly pure PBFB in high yields.

It is a purpose of this invention to provide a simple and economical process for the preparation of highly pure PBFB, in high yields, by the bromination of FB.

It is another purpose of this invention to provide a process which does not require a work-up stage, but in which the crude reaction product goes directly to fractional distillation and the distillation residues are then transferred to the next reaction.

It is a still further purpose of this invention to provide such a process which does not require over-bromination, viz. can be carried out at a molar ratio of bromine to FB of about 1.

It is a still further purpose of this invention to provide such a process which can be carried out with or without the presence of a solvent.

It is a still further purpose of this invention to provide such a process which does not require expensive catalysts.

Other purposes and advantages of the invention will appear as the description proceeds.

SUMMARY OF THE INVENTION

The process according to the invention is characterized in that the bromination of fluorobenzene is carried out with liquid bromine at temperatures below 0° C. The lowest convenient temperature should be used, which is between 0° and –20° C. without solvent (as solidification occurs at lower temperatures) and between –20° C. and –60° C. with a solvent (in which no problems of solidification occur but in which the solvent recovery must be taken into account).

The bromination is preferably carried out with a $Br_2$/FB molar ratio comprised between 1.01 and 1.02.The lower the temperature used, the less OBFB will be produced and thus the less, slight excess of bromine will be required to convert it to DBFB. At the same time the lower the excess bromine, the less PBFB will be converted to DBFB and thus the higher will be the yield. The reaction temperature is thus crucial for obtaining a good yield of high purity PBFB.

A satisfactory catalyst is $FeCl_3$, which is used in an amount of 0.5–2% by weight with respect to the FB.

The reaction can be carried out in the absence of a solvent, or in the presence of a solvent chosen from among dichloromethane (DCM) or dibromomethane (DBM). If a solvent is used, it is used in a weight ratio to the FB of 1:1.

The bromine should be added to the FB at a low temperature, e.g. from 0° C. to the reaction temperature, and the temperature of the reaction mixture should be controlled by efficient cooling to avoid any sudden increases which would lead to a decrease in selectivity.

DETAILED DESCRIPTION OF PREFERRED EMBODIMENTS

According to an embodiment of the invention, the reaction is carried out in the absence of a solvent. Fluorobenzene (FB) is introduced into a reactor provided with a stirrer. $FeCl_3$, in an amount of 0.5–2% by weight of the FB, is added as a catalyst. The FB and the $FeCl_3$, as well as the bromine, should be, as much as possible, free from moisture. An amount of moisture of 0.1% by weight in each reagent should be considered as a maximum. The reactor is cooled to a temperature below 0° C. and desirably close to the chosen reaction temperature. Thereafter, an approximately equimolar (with respect to the FB) quantity of bromine is added under effective stirring, so that the catalyst is homogeneously distributed throughout the reaction mixture. Effective cooling of the reactor is maintained during the entire reaction after which the reactor is heated to ~60° C., in a post-reaction, in order to convert the OBFB to DBFB.

After the post-reaction, distillation is performed on the reaction mixture without any intermediate work-up. Highly pure PBFB is obtained in high yield.

EXAMPLE 1

Preparation of PFBP Without Solvent

FB (1.92 kg, 20 mole) and anhydrous $FeCl_3$ powder (20 g) were placed in a 4-1 reactor equipped with an efficient stirrer, a condenser and a thermometer, and connected to a peristaltic pump. To the top of the condenser was attached a water trap (2 kg distilled water) to absorb HBr and HCl released during the reaction. The $FB/FeCl_3$ mixture was cooled to −20° C. and bromine (3.26 kg, 20.38 mole) was fed in via the peristaltic pump over 2 hours. HBr started to evolve immediately, and the temperature rose. During the addition, the temperature was kept below −15° C. After all the bromine had been added, a sample was taken and analyzed.

The reaction mixture was heated at 60° C. for a further 1 hour with stirring, then another sample was taken and analyzed.

The crude product was distilled under atmospheric pressure using a column 30 cm long and with a 2.2 cm diameter, filled with 0.5 cm Raschig rings. 3.4 kg pure PBFB was obtained at 153°–155° C. in a yield of ~97% and a purity of ≧99.8%.

The distillation residues contain $FeCl_3/FeBr_3$, PBFB and DBFB. The residues can be transferred to an additional reaction by adding FB and bromine, without the need for any additional catalyst.

EXAMPLE 2

Preparation of PFBP With Solvent

FB (0.96 kg, 10 mole), anhydrous $FeCl_3$ powder (10 g) and DCM (dichloromethane, 0.96 kg) were placed in a 4-1 reactor equipped with an efficient stirrer, a condenser and a thermometer, and connected to a peristaltic pump. To the top of the condenser was attached a water trap (1 kg distilled water) to absorb HBr and HCl released during the reaction. The $FB/FeCl_3$ mixture was cooled to −65° C. and bromine (1.62 kg, 10.1 mole) was fed in via the peristaltic pump over 2 hours. HBr started to evolve, and the temperature rose. During the addition, the temperature was kept below −60° C. After all the bromine had been added, a sample was taken and analyzed.

The reaction mixture was heated at 30° C. for a further 2 hours with stirring, then another sample was taken and analyzed.

The solvent was removed by evaporation and recovered for recycling.

The crude product was distilled under atmospheric pressure using a column 30 cm long and with a 2.2 cm diameter, filled with 0.5 cm Raschig rings. 1.72 kg pure PBFB was obtained at 153°–155° C. in a yield of ~98.3%, and with a purity of ≧99.8%.

The distillation residues contain $FeCl_3/FeBr_3$, PBFB and DBFB, and can be recycled to an additional reaction, as above.

The results of the reaction carried out at various temperatures are illustrated in Table I.

TABLE I

| Expt. no. | Reaction | Composition of product before post reaction GC, area % | | | Ratio PBFB/ | Composition of product after post reaction GC, area % | | |
|---|---|---|---|---|---|---|---|---|
| 35968- | temp., °C. | PBFB | OBFB | DBFB | OBFB | PBFB | OBFB | DBFB |
| 22 | 13–15 | 98.20 | 1.80 | (—) | 54.6 | 95.8 | 0.1 | 4.1 |
| 24 | 0–5 | 98.60 | 1.40 | (—) | 70.4 | 96.8 | 0.1 | 3.1 |
| 25 | −20 to −17 | 99.20 | 0.80 | (—) | 124.0 | 97.7 | 0.1 | 2.2 |
| 35 | −22 to −18 | 99.20 | 0.70 | (—) | 141.7 | 97.8 | 0.1 | 2.1 |
| 33* | −45 to −38 | 99.57 | 0.33 | (—) | 301.5 | 98.6 | 0.1 | 1.3 |
| 30* | −65 to −60 | 99.78 | 0.22 | (—) | 453.5 | 99.0 | 0.1 | 0.9 |

*These reactions were carried but in DCM in a w/w ratio of 1:1 FB to DCM. The remaining reactions were carried out without solvent
(—) Not detected (<0.1%)

The data in the table shows that the PBFB/OBFB ratio, which expresses the purity of the final product, is sharply dependent on the temperature.

While embodiments of the invention have been described by way of illustration, it will be apparent that the invention can be carried out by persons skilled in the art with many modifications, variations and adaptations, without departing from its spirit or exceeding the scope of the claims.

I claim:

1. Process for the production of p-bromofluorobenzene with high purity and high yield by the bromination of fluorobenzene, comprising:
    stirring a reaction mixture of fluorobenzene and liquid bromine at temperatures below about −20° C. so that said fluorobenzene and said liquid bromine react to form said p-bromofluorobenzene; and
    maintaining said temperature below about −20° C. during the entire reaction of said fluorobenzene with said liquid bromine.

2. Process according to claim 1, wherein the bromination is carried out with $Br_2$/fluorobenzene molar ratio comprised between 1.01 and 1.02.

3. Process according to claim 1, wherein the bromination is carried out with an approximately equimolar $Br_2$/flourobenzene ratio.

4. Process according to claim 1, wherein the bromination is carried out in the presence of a catalyst.

5. Process according to claim 4, wherein the catalyst is $FeCl_3$.

6. Process according to claim 4, wherein the catalyst is $FeCl_3$, and is used in an amount of 0.5–2% by weight with respect to the fluorobenzene.

7. Process according to claim 1, wherein said reaction mixture further includes dichloromethane or dibromomethane.

8. Process according to claim 9, wherein said dichloromethane or dibromomethane is used in a weight ratio to the fluorobenzene of 1:1.

9. Process according to claim 1, wherein the temperature of the reaction mixture is controlled by efficient cooling to avoid any significant increase thereof.

10. Process according to claim 1, wherein the bromination is carried out under strong stirring.

11. Process according to claim 1, wherein after said reaction of said fluorobenzene and said liquid bromine is complete, said reaction mixture is heated to between about 30° C. and about 60° C. so that any o-bromofluorobenzene present is converted to p-bromofluorobenzene.

12. Process for the production of p-bromoflulorobenzene with high purity and high yield by the bromination of fltuorobenzene, comprising:

stirring a reaction mixture of fluorobenzene and liquid bromine at temperatures below about −38° C. so that said fluorobenzene and said liquid bromine react to form said p-bromoflulorobenzene; and maintaining said temperature below about −40° C. during the entire reaction of said fluorobenzene with said liquid bromine.

13. The process of claim 12, wherein said reaction mixture further includes a solvent.

14. The process for the production of p-bromofluorobenzene with high purity and high yield by the bromination of fluorobenzene, comprising:

stirring a reaction mixture comprising fluorobenzene and liquid bromine in the absence of a solvent at temperatures between about 0° C. and about −20° C. so that said fluorobenzene and said liquid bromine react to form said p-bromofluorobenzene; and maintaining said temperature between about 0° C. and about −20° C. during the entire reaction of said fluorobenzene with said liquid bromine.

* * * * *

UNITED STATES PATENT AND TRADEMARK OFFICE
CERTIFICATE OF CORRECTION

PATENT NO. : 5,847,241
DATED : December 8, 1998
INVENTOR(S) : Oren

It is certified that error appears in the above-identified patent and that said Letters Patent is hereby corrected as shown below:

Column 2, line 44, "FeCI$_3$" should read --FeCl$_3$--.

Column 4, in Table I, line 34, "*These reactions were carried but" should read --*These reactions were carried out--.

Column 5, line 4, "9" should read --7--.

Signed and Sealed this

Thirtieth Day of March, 1999

Attest:

Q. TODD DICKINSON

*Attesting Officer*  *Acting Commissioner of Patents and Trademarks*